US009044486B2

(12) United States Patent
Whittaker et al.

(10) Patent No.: US 9,044,486 B2
(45) Date of Patent: Jun. 2, 2015

(54) METHOD FOR PROPHYLAXIS OR TREATMENT OF FELINE INFECTIOUS PERITONITIS (75) Inventors: Gary R. Whittaker, Ithaca, NY (US); Andrew D. Regan, Athens, GA (US)

(73) Assignee: Cornell University, Ithaca, NY (US)

( * ) Notice: Subject to any disclaimer, the term of this patent is extended or adjusted under 35 U.S.C. 154(b) by 833 days.

(21) Appl. No.: 12/935,967

(22) PCT Filed: Apr. 2, 2009

(86) PCT No.: PCT/US2009/039277
§ 371 (c)(1),
(2), (4) Date: Feb. 22, 2011

(87) PCT Pub. No.: WO2009/124178
PCT Pub. Date: Oct. 8, 2009

(65) Prior Publication Data
US 2011/0142797 A1 Jun. 16, 2011

Related U.S. Application Data (60) Provisional application No. 61/041,700, filed on Apr. 2, 2008.

(51) Int. Cl.
*A61P 31/14* (2006.01)
*A61K 38/55* (2006.01)
*A61K 38/05* (2006.01)

(52) U.S. Cl.
CPC ............... *A61K 38/55* (2013.01); *A61K 38/05* (2013.01)

(58) Field of Classification Search
CPC .................... A61K 38/05; A61K 38/55
See application file for complete search history.

(56) References Cited

U.S. PATENT DOCUMENTS

| 2004/0063093 | A1 | 4/2004 | Miller et al. | |
| 2004/0131628 | A1 | 7/2004 | Bratzler et al. | |
| 2005/0148504 | A1* | 7/2005 | Katunuma et al. | 514/12 |
| 2005/0187192 | A1 | 8/2005 | Fleming et al. | |
| 2005/0267071 | A1* | 12/2005 | Freire et al. | 514/64 |
| 2006/0051744 | A1 | 3/2006 | Austin et al. | |
| 2007/0053878 | A1 | 3/2007 | Haagmans et al. | |
| 2007/0203073 | A1 | 8/2007 | Diamond et al. | |

FOREIGN PATENT DOCUMENTS

WO 2006/076007 A2 7/2006

OTHER PUBLICATIONS

Feline Infectious Peritonitis-ASPCA, from http://www.aspca.org/pet-care/cat-care/feline-infectious-peritonitis, enclosed pp. 1-2, access Aug. 7, 2013.*
Diaz et al, Diagnosis and clinical signs of feline infectious peritonitis in the central nervous system, CVJ, 2009, 50, pp. 1091-1093.*
Geoffrey et al, Inhibition of the Growth of Human Coronavirus 229E by Leupeptin, J. gen. Virol., 1985, 66, pp. 363-366.*
Towatari et al, Novel epoxysuccinyl peptides A selective inhibitor of cathepsin B, in vivo, FEBS Letters, 1991, 280, pp. 311-315.*
Andrew, Feline infectious peritonitis, Vet Clin North Am Small Anim Pract., 2000, 30, pp. 987-1000.*
Woo et al, Coronavirus Diversity, Phylogeny and Interspecies Jumping, Exp Biol Med, 2009, 234, pp. 1117-1127.*
Menzel, et al., Cathepsins B, L and D in Inflammatory Bowel Disease Macrophages and Potential Therapeutic Effects of Cathepsin Inhibition in vivo, Clinican and Experimental Immunology, Oct. 2006, vol. 146, No. 1, pp. 169-180.
Yount, Boyd et al. Reverse genetics with a full-length infectious cDNA of severe acute respiratory syndrome coronavirus, PNAS, Oct. 28, 2003, vol. 100, No. 22, pp. 12995-13000.
Anand, Kanchan et al. Structure of coronavirus main proteinase reveals combination of a chymotrypsin fold with an extra alpha-helical domain, The EMBO Journal, May 5, 2002, vol. 21, No. 13 pp. 3213-3224.
Chandran, Kartik et al. Endosomal Proteolysis of the Ebola Virus Glycoprotein Is Necessary for Infection, Science, Jun. 10, 2005, vol. 308, pp. 1643-1645.
Collins, Arlene et al. Inhibitory Effects of Recombinant Human Cystatin C on Human Coronaviruses, Antimicrobial Agents and Chemotherapy, Nov. 1, 1991, vol. 35, No. 11, pp. 2444-2446.
Follis, Kathryn E. et al. Furin cleavage of the SARS coronavirus spike glycoprotein enhances cell-cell fusion but does not affect virion entry, Virology, Mar. 7, 2006, vol. 350, pp. 358-369.
Goetz, D.H. et al. Substrate Specificity Profiling and Identification of a New Class of Inhibitor for the Major Protease of the SARS Coronavirus, Biochemistry, Jul. 3, 2007, vol. 46, No. 30, pp. 8744-8752.
Groneberg, David A. et al. Molecular mechanisms of severe acute respiratory syndrome (SARS), Respiratory Research, Jan. 20, 2005, vol. 6, No. 8, 16 pages.
Haagmans, Bart L. et al. Coronaviruses and their therapy, Antiviral Research, Jun. 19, 2006, vol. 71, pp. 397-403.
de Haan, C.A.M. et al. Cleavage of Group 1 Coronavirus Spike Proteins: How Furin Cleavage Is Traded Off against Heparan Sulfate Binding upon Cell Culture Adaptation, Journal of Virology, Apr. 9, 2008, vol. 82, No. 12, pp. 6078-6083.
Hegyi, Annette et al. Mutational analysis of the active centre of coronavirus 3C-like proteases, Journal of General Virology, Mar. 1, 2002, vol. 83, pp. 581-593.

(Continued)

*Primary Examiner* — Julie Ha
*Assistant Examiner* — Li Ni Komatsu
(74) *Attorney, Agent, or Firm* — Hodgson Russ LLP (57) ABSTRACT

Provided is a method for treatment and/or prophylaxis of FIP (feline infectious peritonitis) in cats. The method is performed by administering to a cat a composition comprising a therapeutic and/or prophylactic amount of a cysteine protease inhibitor. The cysteine protease inhibitor can be a selective cathepsin B inhibitor. Also provided is a method for inhibiting FIPV (Feline infectious peritonitis virus) replication. The method comprises contacting a cell infected with FIPV with a cysteine protease inhibitor in an amount effective to inhibit replication of FIPV. It is expected the method will be effective for therapy or prophylaxis of FIP in any species of cat and will be effective against any strain of feline coronavirus.

6 Claims, 7 Drawing Sheets

(56) References Cited

OTHER PUBLICATIONS

Leung-Toung, R. et al. Thiol Proteases: Inhibitors and Potential Therapeutic Targets, Current Medicinal Chemistry, Mar. 1, 2006, vol. 13, pp. 547-581.

Shi, J. et al. Dissection Study on the Severe Acute Respiratory Syndrome 3C-like Protease Reveals the Critical Role of the Extra Domain in Dimerization of the Enzyme, The Journal of Biological Chemistry, Mar. 22, 2004, vol. 279, No. 23, pp. 24765-24773.

Yang, H. et al. Drug Design Targeting the Main Protease, the Achilles' Heel of Coronaviruses, Dec. 1, 2006, vol. 12, No. 35, pp. 4573-4590.

Rottier, P.J.M. et al. Acquisition of Macrophage Tropism during the Pathogenesis of Feline Infectious Peritonitis Is Determined by Mutations in the Feline Coronavirus Spike Protein, Nov. 1, 2005, vol. 79, No. 22, pp. 14122-14130.

* cited by examiner

METHOD FOR PROPHYLAXIS OR TREATMENT OF FELINE INFECTIOUS PERITONITIS

This application claims priority to U.S. application Ser. No. 61/041,700, filed on Apr. 2, 2008, the disclosure of which is incorporated herein by reference.

This invention was made with government support under Grant No. T32AI007618 awarded by the National Institutes of Health. The government has certain rights in the invention.

FIELD OF THE INVENTION

The present invention relates generally to the field of animal health, and in particular to methods for the prophylaxis and treatment of Feline infectious peritonitis.

BACKGROUND OF THE INVENTION

Group I feline coronavirus (FCoV) infections are common in cats usually cause only mild and often inapparent enteritis; in these cases the virus is classified as feline enteric coronavirus (FECV) (de Groot-Mijnes, J. D., et al., (2005) J Virol 79, 1036-1044; Haijema et al., 2007). However, feline infectious peritonitis (FIP) is a highly lethal systemic infection of cats caused by an FCoV classified as Feline infectious peritonitis virus (FIPV) (Haijema, et al. (2007) Molecular and Cellular Biology. Caister Academic Press, Norfolk, UK, pp. 183-203; Olsen, (1993) Vet Microbiol Vol. 36, pp. 1-37). There is currently no treatment available for FIP.

FCoVs exist as two major serotypes, with both type I and type II having the capacity to make the switch from FECV to FIPV. The prevalence of type I and type II within the cat population can vary; type I is the most prevalent, with type II viruses accounting for anywhere between 5 and 30% of viruses isolated. Like all known coronaviruses (CoV), both FIPV and FECV have a distinctive set of club-shaped spikes on their envelope, the spikes being comprised of the viral spike protein (S). The S protein is involved in determining the distinct cellular tropisms exhibited by FIPV and FECV (Rottier, P. J., et al. (2005) J Virol 79, 14122-14130), but the etiology of FIP and the role of S protein in it is not currently understood. It is known that cysteine protease mediated cleavage of coronavirus proteins, including cleavage of the S protein of some coronaviruses, is involved in the infection and replication processes of CoV. For example, U.S. patent application no. 2007/0203073 includes an analysis of the specificity of endosomal cysteine proteases in mediating SARS-CoV infection and cleavage of SARS-CoV S protein and found that the cysteine protease cathepsin L, but not cathepsin B, plays a critical role in SARS-CoV S protein-mediated viral entry. Other researchers (Collins, et al. (1991) Antimicrobial Agents And Chemotherapy, Vol. 35, pp 2444-2446) have determined that cystatin C, which is a potent inhibitor of cathepsin B, inhibited replication of a human coronaviruses, but not a murine coronavirus (A59). It was indicated that the lack of inhibition of murine coronavirus by cystatin C could be because, like FIPV, A59 murine CoV spreads via fusion with the plasma membranes of uninfected cells. It was also suggested that this could explain the observation that leupeptin, a serine and cysteine protease inhibitor, inhibits human coronavirus, but does not strongly inhibit A59 murine coronavirus or FIPV (Collins, et al. (1991). Thus, given the uncertainty about the molecular details of FCoV infection and replication, and the lack of any available FIP treatment, there is an ongoing need to develop methods for prophylaxis and/or treatment of FIP.

SUMMARY OF THE INVENTION

The present invention provides a method for treatment and/or prophylaxis of FIP in cats. The method comprises administering to a cat in need of FIP prophylaxis or therapy a composition comprising a therapeutic and/or prophylactic amount of a cysteine protease inhibitor.

Also provided is a method for inhibiting FIPV replication in a cell. The method comprises contacting a cell infected with FIPV with a cysteine protease inhibitor in an amount effective to inhibit replication of the FIPV.

It is preferred that the cysteine protease inhibitors used in the invention are inhibitors of cysteine cathepsin(s). Any cysteine cathepsin inhibitor is expected to be suitable for use in the invention, and a variety of cysteine cathepsin inhibitors are known in the art and are commercially available. The cysteine cathepsin inhibitor used in the invention can be capable of inhibiting a range of cysteine cathepsins. Combinations of distinct cysteine cathepsin inhibitors can also be used in the invention. In one embodiment, the composition used in the method of the invention comprises a selective inhibitor of cathepsin B.

The compositions used in the method can include any pharmaceutically acceptable carriers, excipients or stabilizers, and may include any other agent that is advantageous for therapy or prophylaxis of viral infections.

The method of the invention can be performed by administration of a composition comprising a cysteine protease inhibitor to a cat via any suitable route, including without limitation parenteral, subcutaneous, intraperitoneal, intrapulmonary, and intranasal routes.

The administrations can be performed as a single dose or in multiple doses. The compositions can be administered prior to exposure to FIPV or FECV, during exposure, after exposure, or in any combination of such time points.

It is expected that the method will be effective at prophylaxis or treatment of FIP in any type of cat and against any strain of FIPV or FECV.

BRIEF DESCRIPTION OF THE FIGURES

FIG. 1 demonstrates the effect of cysteine protease inhibitors on the growth of FIPV-1146 and FECV-1683. A-72 cells were pretreated with specified inhibitors at a concentration of 10 µM and then infected with virus. 3 hours post-infection, fresh media without inhibitor was added to cells and 9 hours post-infection media was collected. Production of extracellular virus from at least three independent experiments was determined by $TCID_{50}$ assay. Error bars represent the standard deviation of the mean. Inhibitors are the cell-permeable irreversible cysteine protease inhibitor E-64d, inhibitors of cathepsin B (CA074-Me), cathepsin L (Z-FY-(tBu)-DMK) and cathepsin K (Boc1).

FIG. 2 demonstrates the effect of cathepsin L and cathepsin B inhibitors on the entry of FIPV-1146 and FECV-1683. A-72 cells were pretreated with the cathepsin L inhibitor Z-FY(tBu)-DMK (CatL-I) or the cathepsin B inhibitor CA074-Me (CatB-I) at the concentration specified, and then infected with virus. 6 hours post-infection cells were fixed and stained for immunofluorescence microscopy with the anti-FCoV nucleocapsid mAb 17B7.1 (FIG. 2A). Images from at least three independent experiments were processed and quantified (FIG. 2B). To control for non-specific effects on replication, cells were also treated with inhibitors 1 h post-infection. For quantification, >1000 cells were scored from three independent replicates of each experimental condition. Error bars represent the standard deviation of the mean.

FIG. 3 demonstrates the effect of lysosomotropic agents on the entry of FIPV-1146 and FECV-1683. A-72 cells were pretreated with NH₄Cl or bafilomycin A at the specified concentration and then infected with virus. 6 hours post-infection cells were fixed and stained for immunofluorescence microscopy with the anti-FCoV nucleocapsid mAb 17B7.1 (FIG. 3A). Images from at least three independent experiments were processed and quantified (FIG. 3B). To control for non-specific effects on replication, cells were also treated with lysomotrophic agents 1 h post-infection. For quantification, >1000 cells were scored from three independent replicates of each experimental condition. Error bars represent the standard deviation of the mean.

FIG. 4 demonstrates the effects of cathepsin L and cathepsin B inhibitors, and low pH, on the infection of feline cells by serotype II FCoVs. CRFK, AK-D or Fc2Lu cells were pretreated with either 10 uM cathepsin B inhibitor CA074-Me (CatB-I), 10 uM cathepsin L inhibitor Z-FY(tBu)-DMK (CatL-I), or 10 mM NH4Cl, and then infected with virus. 6 hours post-infection cells were fixed and stained for immunofluorescence microscopy with the anti-FCoV nucleocapsid mAb 17B7.1. Images from at least three independent experiments were processed and quantified. For quantification >500 cells were scored from three independent replicates. Error bars represent the standard deviation of the mean.

FIG. 5 demonstrates cleavage of FIPV-1146 and FECV-1683 by purified cathepsins. Concentrated virus preparations were incubated with purified cathepsin B, cathepsin L, or buffer alone for 1 h at 37° C., followed by treatment with PNGase F (FIG. 5A). Samples were then analyzed by western blot with the anti-FCoV spike mAb 22G6.4 (FIG. 5B). Quantification of western blot to show degree of cleavage.

FIG. 6 demonstrates the effect of cathepsin inhibitors on the infection of primary feline blood monocytes. Monocytes were purified from the blood of SPF cats, pretreated with the cathepsin B inhibitor CA074-Me (CatB-I) or the cathepsin L inhibitor Z-FY(tBu)-DMK (CatL-I) at a concentration 10 μM, and infected with virus. 12 h post-infection, cells were fixed and stained for immunofluorescence microscopy with the anti-FCoV nucleocapsid mAb 17B7.1 (FIG. 6B). Images from at least three independent experiments were processed and quantified (FIG. 6A). For quantification, >200 cells were scored from three independent replicates of each experimental condition. Error bars represent the standard deviation of the mean.

DESCRIPTION OF THE INVENTION

The present invention provides a method for treatment and/or prophylaxis of FIP in cats. The method comprises administering to a cat in need of treatment or prophylaxis for FIP a cysteine protease inhibitor in an amount effective for treatment and/or prophylaxis of the FIP. The invention takes advantage of our discovery that a selective cathepsin B inhibitor can inhibit propagation of both FIPV and FECV in vitro, as well as inhibit FIPV infection of primary feline blood monocytes.

As used herein, "prophylaxis" means completely or partially preventing formation of one or more symptoms of FIP. "Treatment" of FIP occurs when the severity of one or more FIP symptoms exhibited by a cat infected with FIPV is reduced, and/or when the amount of FIPV in a cat is reduced.

FIP symptoms include otherwise unexplained loss of appetite, weight loss, and chronic fluctuating fever that is unresponsive to antibiotics or corticosteroids. The duration of such symptoms prior to death is usually three to six weeks. Over this period, in about 80-85% of FIP cases, effusion of fluids results in fluid build-up in the abdomen (Hartmann, et al. J. Vet. Med. (2003) Vol. 17, pp 781-790). Effusion can be detected by physical examination, or by using radiography or ultrasound. Thus, a reduction in effusion in a cat infected with FIPV is considered a reduction in a FIP symptom according to the invention. Effusion caused by FIP infection can cause peritoneal inflammation, which can involve the gastrointestinal tract, hepatobiliary system, or pancreas, and can result in vomiting, diarrhea, and icterus. Accordingly, prevention or reduction in any of peritoneal inflammation, vomiting, diarrhea, or icterus in a cat infected with FIPV is also considered a prevention or reduction of an FIP symptom.

Treatment of FIP according to the method of the invention can cause a reduction in FIPV in a cat. Methods for determining the amount of FIPV in cats are known, such as by performing quantitative FIPV nucleic acid amplification in biological samples obtained from a cat. For example, RT-PCR analysis of FIPV RNA can be performed using serum or effusion obtained from a cat (see, e.g., Hartmann, et al. (2003)). Quantitative immunoassays, such as ELISAs performed using antibodies directed to FIPV proteins, can also be used.

In one embodiment, the invention provides a method for inhibiting FIPV replication in one or more feline cells. The method comprises contacting one or more feline cells infected by FIPV with a cysteine protease inhibitor. A reduction in FIPV replication can be determined by routine methods. For example, a reduction in FIPV genomic RNA or FIPV encoded proteins is considered evidence of reduced FIPV replication.

It is expected that the invention will be suitable for treatment or prophylaxis of FIP in any cat, including but not limited to domestic house cats, lynx, bobcats, African lions, mountain lions, cheetahs, tigers, ocelots, jaguars and leopards. It is also expected that the method will be suitable for use against any serotype or strain of FECV or FIPV.

In performance of the method of the invention, any suitable cysteine protease inhibitor can be administered to the cat. Cysteine protease inhibitors are well known in the art and are commercially available. For example, a variety of cysteine protease inhibitors are commercially available from Calbiochem (Gibbstown, N.J.). The inhibitors may be reversible or irreversible inhibitors. The cysteine protease inhibitor used in the invention can be capable of inhibiting a range of distinct cysteine proteases. Additionally, combinations of inhibitors capable of inhibiting distinct cysteine proteases can be used in the invention.

The reference of Frlan, et al. (Current Medicinal Chemistry (2006) 13, 2309-2327), the disclosure of which is incorporated herein by reference, describes a variety of suitable cathepsin B inhibitors. These fall into the classifications of Epoxysuccinyl Cathepsin B Inhibitors, Aziridine Cathepsin B Inhibitors, 1,2,4-Thiadiazole Cathepsin B Inhibitors, Acyloxymethylketone Cathepsin B Inhibitors, β-Lactam Cathepsin B Inhibitors, Organotellurium (IV) Inhibitors of Cathepsin B, Aldehyde Cathepsin B Inhibitors, Ketone Cathepsin B Inhibitors, Cyclopropenone Cathepsin B Inhibitors and Nitrile Cathepsin B Inhibitors.

In one embodiment, the cysteine protease inhibitor used in the invention is a selective inhibitor of cathepsin B. Proteases referred to herein as "cathepsins" refer to cysteine cathepsins (as opposed to the aspartic proteases that are sometimes also referred to in the art as cathepsins). As used herein, the term "selective inhibitor of cathepsin B" means a cathepsin B inhibitor that exhibits greater inhibition of cathepsin B than at least one of cathepsin K, L, H and S. The selective inhibitor of cathepsin B may therefore exhibit less or no detectable inhibition of one or more of K, L, H or S cathepsins. Cysteine protease inhibitors, including selective cathepsin B inhibitors that are suitable for use in the invention, and methods for making such inhibitors, are described in U.S. Pat. Nos. 5,374,623, 5,66,3380, 6,004,933, 6,812,237, 7,008,938, and 7,012,075, the disclosures of each of which are incorporated herein by reference. Selective cathepsin B inhibitors are also commercially available, such as from Calbiochem (Gibbstown, N.J.).

Methods for analyzing inhibition of proteases by protease inhibitors are well known in the art. U.S. Pat. No. 7,008,938, the disclosure of which is incorporated herein by reference, describes some suitable methods for measuring inhibitor activities.

In one embodiment, inhibition can be analyzed by determining the inhibitor's half maximal inhibitory concentration ($IC_{50}$) value for inhibition of one or more particular cysteine proteases, such as cathepsins. Determinations of $IC_{50}$ values are well within the purview of those skilled in the art. Further, $IC_{50}$ values can be utilized in a variety of well known analytic techniques for assessing inhibitor properties, such as calculation of Ki values.

In the present invention, when a selective cathepsin B inhibitor is used, the selective cathepsin B inhibitor can have an $IC_{50}$ value for cathepsin B of less than 1 mM, less than 500 nM, less than 400 nM, less than 300 nM, less than 200 nM, less than 100 nM, less than 75 nM, less than 50 nM, less than 25 nM, less than 15 nM, less than 10 nM, less than 5 nM, or less than 2 nM. The selective cathepsin B inhibitor can have an $IC_{50}$ value that is lower for cathepsin B than for at least one of K, L, H or S cathepsins. For example, the inhibitor is L-3-trans-(Propylcarbamoyl)oxirane-2-carbonyl]-isoleucyl-L-proline, which is generally referred in the art as CA074, has a published $IC_{50}$ of 1.94 nM for cathepsin B, but has an $IC_{50}$ of 233,000 nM for cathepsin L (Frlan, et al. Current Medicinal Chemistry (2006) 13, 2309-2327). The methyl ester of CA074 (L-3-trans-(Propylcarbamoyl)oxirane-2-carbonyl]-isoleucyl-L-proline Methyl Ester), generally referred to as CA074-Me, is also a suitable selective cathepsin B inhibitor, and has improved cell permeability relative to CA074. Both CA074 and CA074-Me are members of the Epoxysuccinyl inhibitor family.

The degree of inhibition of a cysteine protease by an inhibitor can also be represented by the inhibitor's second order rate constant of inactivation, which is represented as $k_{inact}/K_i$ or as $k_2/K_i$. (See, e.g., Bromine et al., Biol. Chem. 375:343-347 (1994); Palmer et al., J. Med. Chem. 38:3193-3196 (1995); Bromme et al., Biochem. J. 315:85-89 (1996)). Methods for determining second order rate constants of inactivation are well known in the art. In one embodiment, the selective cathepsin B inhibitor used in the method of the invention can have a second order rate constant of inactivation for cathepsin B that is greater than the corresponding rate constant for at least one of cathepsins K, L, H, and S. The reference of Powers et al., Chem. Rev., 2002, 102 (12), 4639-4750, the disclosure of which is incorporated herein by reference, provide a review of a variety of inhibitors of cysteine proteases and discloses that the apparent second order rate constant of CA074-Me for cathepsin B is 201 M-1s-1 and 85 M-1s-1 for cathepsin L.

The cysteine protease inhibitors can be prepared for administration by combining them with any suitable pharmaceutically acceptable carriers, excipients and/or stabilizers. Some suitable examples of pharmaceutically acceptable carriers, excipients and stabilizer can be found in *Remington: The Science and Practice of Pharmacy* (2005) 21st Edition, Philadelphia, Pa. Lippincott Williams & Wilkins. Further, any suitable delivery vehicle can be used in the invention, such as a controlled release delivery formulation in which the inhibitor is released over a period of time.

The method of the invention can be performed by administering a composition comprising the cysteine protease inhibitor to a cat using any suitable route of administration, including but not limited to parenteral, subcutaneous, intraperitoneal, intrapulmonary, and intranasal and intraocular routes. Parenteral infusions include intramuscular, intravenous, intraarterial, intraperitoneal, or subcutaneous administration.

The method of the invention can be performed prior to development of FIP, at any point during a period that a cat has FIP, after FIP symptoms have subsided, and combinations thereof. Since the duration of FIP symptoms prior to death is usually three to six weeks, administrations of a composition comprising a cysteine protease inhibitor according to the invention can be performed over periods of three to six weeks (or for shorter or longer times as necessary). For example, the administrations could be performed within minutes or hours upon recognition of a cat exhibiting FIP or because of a known exposure to a FCoV, and continued for between one to seven days, or for two weeks, for three weeks, for four weeks, for five weeks, or for six weeks, or longer, until the FIP symptoms have subsided.

Exposure to FECV or FIPV can place a cat at risk for developing FIP. An exposure to FECV of FIPV could arise, for example, in a setting wherein multiple cats are kept or come into proximity with each other, such as a zoo, a pet store, a multiple cat household, an animal welfare housing facility, a boarding cattery, or a breeding cattery, etc., when a cat kept therein is diagnosed or suspected of having FIP, and/or FECV or FIPV infection. Diagnosis or suspicion of FIP, FECV or FIPV infection in one or more cats in such settings would therefore place the other cats at risk for FIP, and in need of FIP prophylaxis. In such situations, administration of the cysteine protease inhibitor to the non-infected cats can be performed to achieve a prophylactic effect, while the cat(s) that is diagnosed or suspected of having FIP, and/or FECV or FIPV infection could be treated therapeutically. For prophylactic purposes, it is preferable to administer the cysteine protease inhibitor to the cat at risk for developing FIP prior to exposure to FECV or FIPV, or to exposure to a cat diagnosed with or suspected of having FIP. However, cats infected with FECV can also be at risk for developing FIP via in vivo conversion of FECV to FIPV, and can therefore also be treated prophylactically.

Suitable dosages of the cysteine protease inhibitor administered according to the method of the invention for either therapeutic or prophylactic purposes can be determined by those skilled in the art and will be based, at least in part, on consideration of the species of cat, the cat's age, sex, size, and health, the particular inhibitor used, the type of delivery system used, the time of administration relative to the stage of FIP or the degree of risk of being infected with an FCoV, and whether a single, multiple, or controlled release dose regimen is to be employed.

Selective administration of the cathepsin B inhibitor CA-074-Me at 10 mg/kg has been indicated to inhibit cathepsin B in a mouse (Van Acker et al., Am J Physiol Gastrointest Liver Physiol (2002) 283: G794-G800). Without intending to be bound by any particular theory, it is therefore expected that administration of a selective cathepsin B inhibitor to a cat would also result in inhibition of lysosomal cathepsin B, which is believed to be necessary for inhibition of FIPV cell entry and replication. In this regard, for selective cathepsin B inhibitors, it is expected that dosages of between 1 and 100 (inclusive, and including all integers between 1 and 100) mg/kg body weight per day will be an effective amount for treatment or prophylaxis of FIP. In varying embodiments, the selective cathepsin B inhibitor can be administered as 5 mg/kg/day, 10 mg/kg/day, 15 mg/kg/day, 20 mg/kg/day, or 25 mg/kg/day.

The inhibitors can be delivered in conjunction with any conventional anti-viral treatment regimen, including sequential or simultaneous administration of anti-viral agents, passive immunotherapies, vaccines, adjuvants, anti-inflammatories, interferons, and the like. For example, passive immunotherapy using anti-FIPV antibodies, or administration of steroids, such as prednisolone or prednisone, or administration of interferons (IFN) using techniques known to those skilled in the art can each be used in connection with the method of the invention.

The following Examples are intended to illustrate but not limit the invention.

Example 1

This Example describes the Materials and Methods used to obtain the data presented in the Examples that follow below.

Cell Lines and Primary Feline Monocytes

Crandell-Rees Feline Kidney (CRFK) cells and feline fetal lung cells (AK-D) were obtained from the American Type Culture Collection (ATCC). A-72 cells were provided by Dr. Colin Parrish (Cornell University, Baker Institute for Animal Health). Fc2Lu cells were provided by Dr. Ed Dubovi (Animal Health Diagnostic Center, New York State College of Veterinary Medicine, Cornell University.). Primary feline monocytes were individually purified from the blood of three SPF cats (Liberty Research Inc., Waverly, N.Y.) using a standard Ficoll-paque gradient (GE Healthcare) as specified by the manufacturer. Monocytes were seeded in 24-well plates and allowed to attach to culture-treated glass coverslips overnight. After washing, the purity of monocyte preparations was checked by immunofluorescence microscopy using the monocyte marker DH59B. CRFK, Fc2Lu, AK-D and A-72 cells were grown in the presence of 5% CO2 at 37° C. in RPMI-1640 media pH 7.4 supplemented with 10% Fetal Bovine Serum (FBS), 2 mM glutamine, 100 U/ml penicillin and 10 ug/ml streptomycin. Monocytes were cultured under the same conditions except the media was supplemented with 20% FBS.

Viruses and Antibodies

FIPV WSU 79-1146 (FIPV-1146) was obtained from the ATCC. FECV WSU 79-1683 (FECV-1683) and FIPV-DF2 were provided by Dr. Ed Dubovi (Animal Health Diagnostic Center, New York State College of Veterinary Medicine, Cornell University). FIPV-1146 and FECV-1683 were grown in A-72 cells and FIPV-DF2 was grown in CRFK cells, and supernatant collected after cytopathic effect (CPE) was observed in 80% of cells. Supernatant was clarified by a low speed centrifugation step (1,250×g for 10 min) and viral particles were then pelleted by centrifugation at 28,000 rpm in a SW28 rotor (Sorvall) for 60 min. Pellets were resuspended in either phosphate-buffered saline pH 7.4 for infection assays, or acetate buffer pH 5.0 for cathepsin cleavage assays. Virus titers were determined with TCID50 assays on CRFK cells, using standard techniques (Gray, 1999). Anti-FCoV nucleocapsid (17B7.1) (Olsen et al., 1992) and spike 22G6.4 monoclonal antibodies were provided by Dr. Ed Dubovi (Animal Health Diagnostic Center, New York State College of Veterinary Medicine, Cornell University). The monocyte marker antibody (anti-CD127a mAb DH59B) was obtained from Veterinary Medical Research & Development, Inc. (Pullman, Wash.).

Inhibitors

The cysteine protease inhibitor (2S,3S)-trans-Epoxysuccinyl-L-leucylamido-3-methylbutane ethyl ester loxistatin (E-64d), the cathepsin B inhibitor [L-3-trans-(Propylcarbamoyl)oxirane-2-carbonyl]-L-isoleucyl-L-proline Methyl Ester (CA074-Me), the cathepsin K inhibitor 1-(N-Benzyloxycarbonyl-leucyl)-5-(N-Boc-phenylalanyl-leucyl)carbohydrazide (Boc-1) and bafilomycin A1 were purchased Calbiochem (San Diego, Calif.). The cathepsin L inhibitor Z-Phe-Tyr(t-Bu)-diazomethylketone (Z-FY(t-Bu)-DMK) was purchased from Axxora (San Diego, Calif.).

Growth and Infection Assays

For growth assays, A-72 cells were seeded to 75% confluency on 24-well tissue culture-treated plates. Cells were preincubated with specified treatments in serum-free media for 60 min before addition of virus to a final concentration of 106TCID/ml. After 3 hours, cells were washed and media replaced with fresh serum-free media. After 9 hours, supernatant was collected and frozen at −80° C. until later determination of viral titer by TCID50 assay. For infection assays, cells were seeded to 75% confluency on 24-well plates with tissue culture-treated glass coverslips. Cells were treated with inhibitors as specified, either 60 min before, or 60 min after the addition of virus. Virus was added to a final concentration of 106TCID/ml, which infected 20-50% of control cells under the conditions tested. 6 hours post-infection, cells were fixed in 3% paraformaldehyde and stained with the anti-FcoV nucleocapsid mAb 17B7.1, essentially as described previously (Chu et al., 2006). Influenza virus and Sendai virus infection assays were performed as previously described (Chu et al., 2006). All assays were repeated at least three times and 8-15 widefield images were captured and quantified per experimental replicate. Cells were viewed on a Nikon Eclipse E600 fluorescence microscope, and images were captured with a Sensicam EM camera and IPLab software before transfer into ImageJ software (<rsb.info.nih.gov/ij/>) for determination of infection frequency.

Cleavage Assays and Western Blot Analysis

Concentrated viral particles (1012TCID/ml) were suspended in acetate buffer pH 5.0. 50 μl of virus preparation was incubated with either purified cathepsin L (Calbiochem, San Diego Calif.) or purified cathepsin B (Calbiochem, San Diego Calif.) at a final concentration of 1 μM for 1 hour at 37° C., followed by the addition of 500 U PNGase F (New England Biolabs, Ipswich Mass.) to allow differentiation of any multiply glycosylated species. SDS sample buffer was added and the reaction was heated at 95° C. before separation using a 4-20% SDS-PAGE gel at 200V for 2 hours. Gels were electroblotted to PVDF membrane, blocked with 5% bovine serum albumin and probed with the anti-FcoV spike protein mAb 22G6.4. Membranes were developed using anti-mouse antibody linked to horseradish peroxidase (SouthernBiotech, Birmingham Ala.) and ECL substrate (Pierce, Rockford Ill.) and images captured using a Fujifilm LAS-3000 CCD camera. Western blot densitometry analysis of spike protein cleavage was performed using ImageJ software. Percent cleavage was determined by dividing pixel intensity of the cleaved spike protein band by total pixel intensity of the cleaved and uncleaved spike protein bands combined.

Example 2

This Example describes effect of cysteine proteases on the propagation of FIPV-1146 and FECV-1683 in vitro. FIPV-1146 and FECV-1683 are genotypically very similar and are known to share a high degree of amino acid identity in their spike protein (>95%) yet cause radically different clinical outcomes—lethal vasculitis for FIPV-1146, compared to mild enteritis for FECV-1683.

Figure 1:
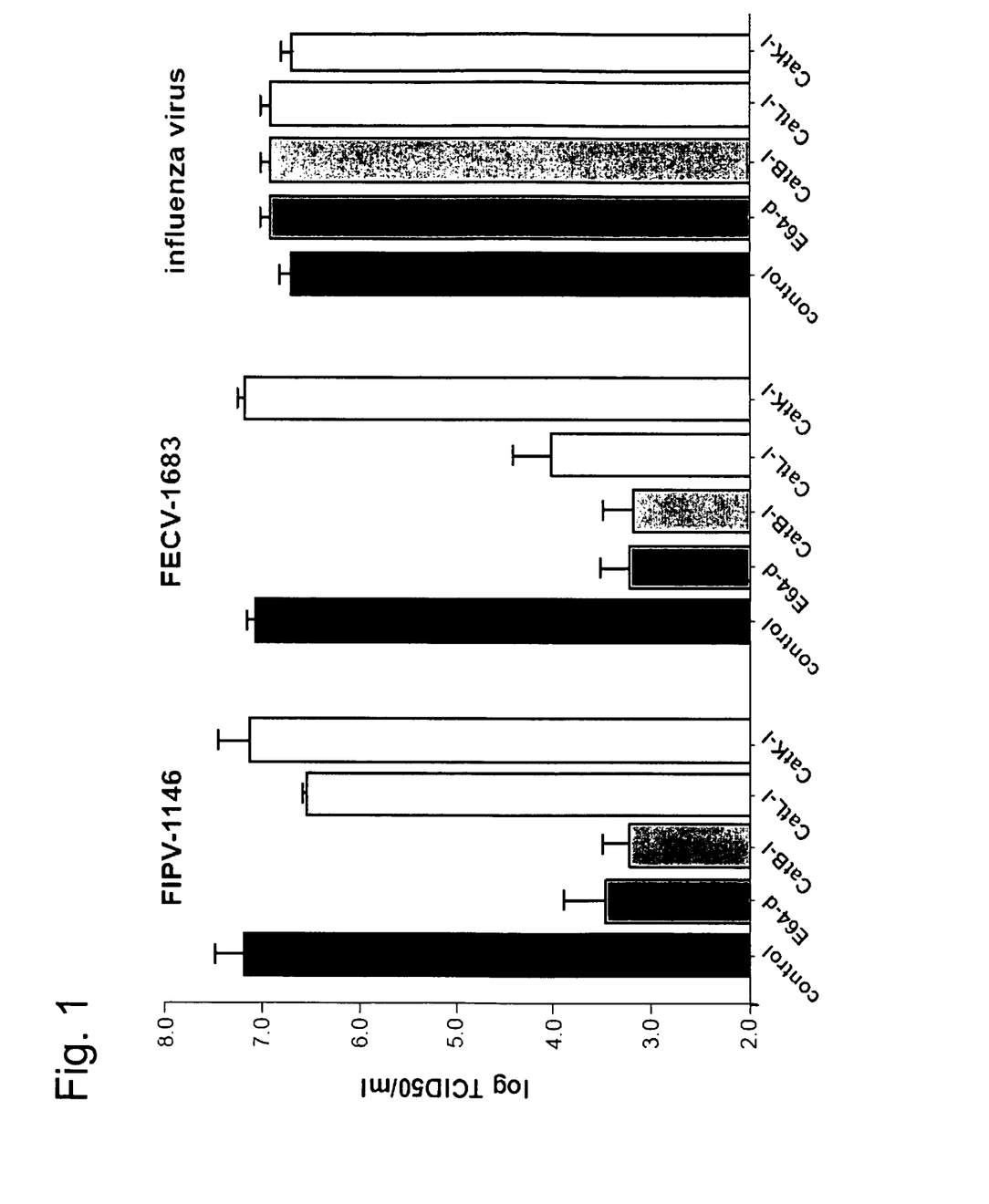

To determine the role of cysteine proteases in the life cycle of FIPV-1146 and FECV-1683, we first pre-treated A-72 cells with the cell-permeable irreversible cysteine protease inhibitor E-64d, which non-selectively inhibits a range of cysteine proteases. Cells were then infected with either FIPV-1146 or FECV-1683. As a control, cells were infected with influenza virus, which is not believed to require proteolytic activation by cysteine proteases during entry. We collected cell supernatants at 9 h post-infection and assayed virus production by TCID50 assay. Pretreatment with E-64d significantly reduced the production of both FIPV-1146 and FECV-1683 viral particles, as compared to control cells pretreated with DMSO alone (FIG. 1). As expected, E-64d had no effect on influenza virus infection.

To further investigate the potential roles of cathepsins in the growth of FIPV-1146 and FECV-1683, cells were then pretreated with selective inhibitors of cathepsin B (CA074-Me), cathepsin L (Z-FY-(tBu)-DMK) and cathepsin K (Boc1). As shown in FIG. 1, the cathepsin B inhibitor considerably limited the production of both FIPV-1146 and FECV-1683. In contrast, the cathepsin L inhibitor had only a negligible effect on FIPV-1146; however it greatly diminished the propagation of FECV-1683. Cathepsin K inhibitor had no significant effect on either virus (FIG. 1). The selective cathepsin inhibitors also had no effect on influenza virus infection. These data indicate that both FIPV-1146 and FECV-1683 require cathepsin B activity for propagation, whereas FECV-1683 selectively requires cathepsin L activity.

Example 3

Figure 2A:
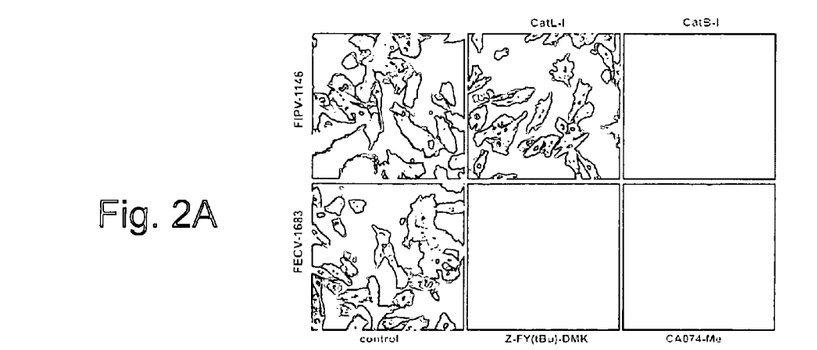
Figure 2B:
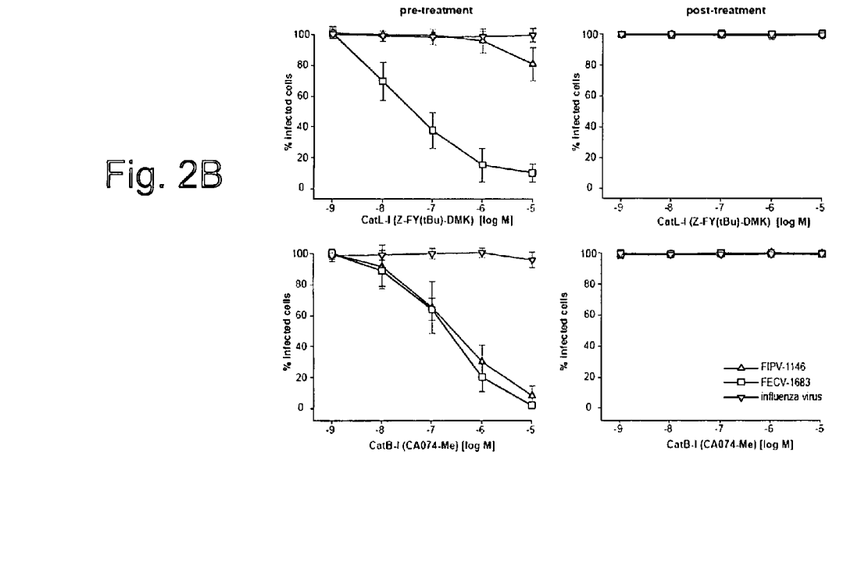

This Example provides an analysis of the role of cathepsin B and L during entry of FIPV-1146 and FECV-1683 into host cells. To establish if the effects of the cathepsin B and L inhibitors occurred during virus entry, A-72 cells were treated with five log dilutions of inhibitor either 60 min pre-infection, or 60 min post-infection, and then infected with FIPV-1146 or FECV-1683. Cells were fixed 6 hours post-infection, and infected cells were detected by immunofluorescence microscopy using the anti-FcoV nucleocapsid monoclonal antibody 17B7.1, and quantified (FIG. 2). Pre-incubation with the selective cathepsin B inhibitor almost completely blocked infection by FIPV-1146, however treatment after entry had no effect (FIG. 2). Consistent with data from viral growth assays, the cathepsin L inhibitor had no effect on FIPV-1146 entry, except for some limited effect at the highest concentration tested (FIG. 2B). Pre-incubation with either cathepsin B or cathepsin L inhibitor both potently blocked infection by FECV-1683, and again treatment after entry with either inhibitor had no effect. As a control, cells were treated with inhibitors and infected with influenza virus. Infected cells were fixed 6 hours post-infection and detected by immunofluorescence microscopy with the anti-influenza nucleoprotein monoclonal antibody H19 (FIG. 2). Neither the cathepsin B nor the cathepsin L inhibitor had an effect on influenza virus entry. Pretreatment with the cathepsin K inhibitor had no effect on the cellular entry of either FIPV-1146, FECV-1683 or influenza virus (data not shown). These data show that the inhibitory effects of the cathepsin inhibitors are manifested during virus entry.

Example 4

Figure 3A:
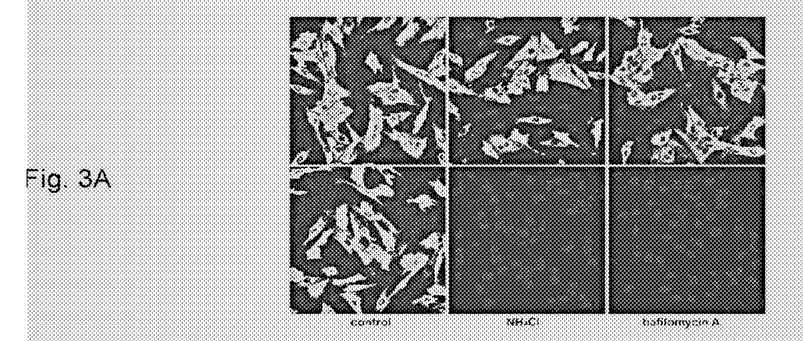
Figure 3B:
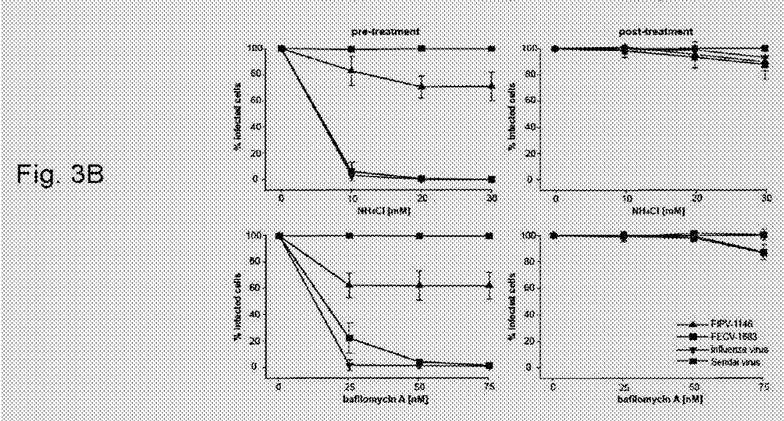

This Example demonstrates the effect of lysosomotropic agents on the cellular entry of FIPV-1146 and FECV-1683. In connection with this, lysosomotropic agents such as $NH_4Cl$ and bafilomycin A are well established to disrupt the acidic environment of endocytic compartments. To assess the role of low pH during entry of FIPV-1146 and FECV-1683, A-72 cells were pretreated with either $NH_4Cl$ or bafilomycin A1. We first assessed the effect of $NH_4Cl$, a weak base that acts to neutralize the low pH of the endosome. Pre-treatment with 10 mM $NH_4Cl$ only partially inhibited entry of FIPV-1146 (approximately 20% inhibition), however the same concentration almost completely blocked entry by FECV-1683 (FIG. 3). Even following pre-treatment with 30 mM $NH_4Cl$, FIPV-1146 entry was only partially blocked as compared to FECV-1683. As controls for these experiments, we used influenza virus and Sendai virus. Influenza virus is well established to require low pH to trigger its fusion mechanism and was completely inhibited by pretreatment with 10 mM $NH_4Cl$, analogous to the results obtained with FECV-1683 (FIG. 3). Sendai virus is known to fuse at a neutral pH and accordingly showed no reduction in entry with cell pretreated with $NH_4Cl$ (FIG. 3).

We next assessed the effect of bafilomycin A1, an inhibitor of the vacuolar-type $H^+$-ATPase. Pretreatment of cells with 50 nM bafilomycin A1 completely blocked entry of both FECV-1683 and influenza virus, but only partially blocked entry by FIPV-1146 (approximately 40% inhibition). Sendai virus entry was unaffected by bafilomycin A1 at the concentrations tested. Treatment after entry with both $NH_4Cl$ and bafilomycin A1 had a minimal effect on FIPV-1146 and FECV-1683 at the concentrations shown in FIG. 3, however higher concentrations (>100 nM bafilomycin A1 and >30 mM $NH_4Cl$) were able to significantly reduce infectivity of both viruses (data not shown). Post-treatment with bafilomycin had no effect on influenza or Sendai virus infection at the concentrations shown in FIG. 3. Overall these data show that FECV-1683 entry is highly dependent on low endosomal pH, whereas FIPV-1146 is much less dependent on low pH during entry.

Example 5

Figure 4:
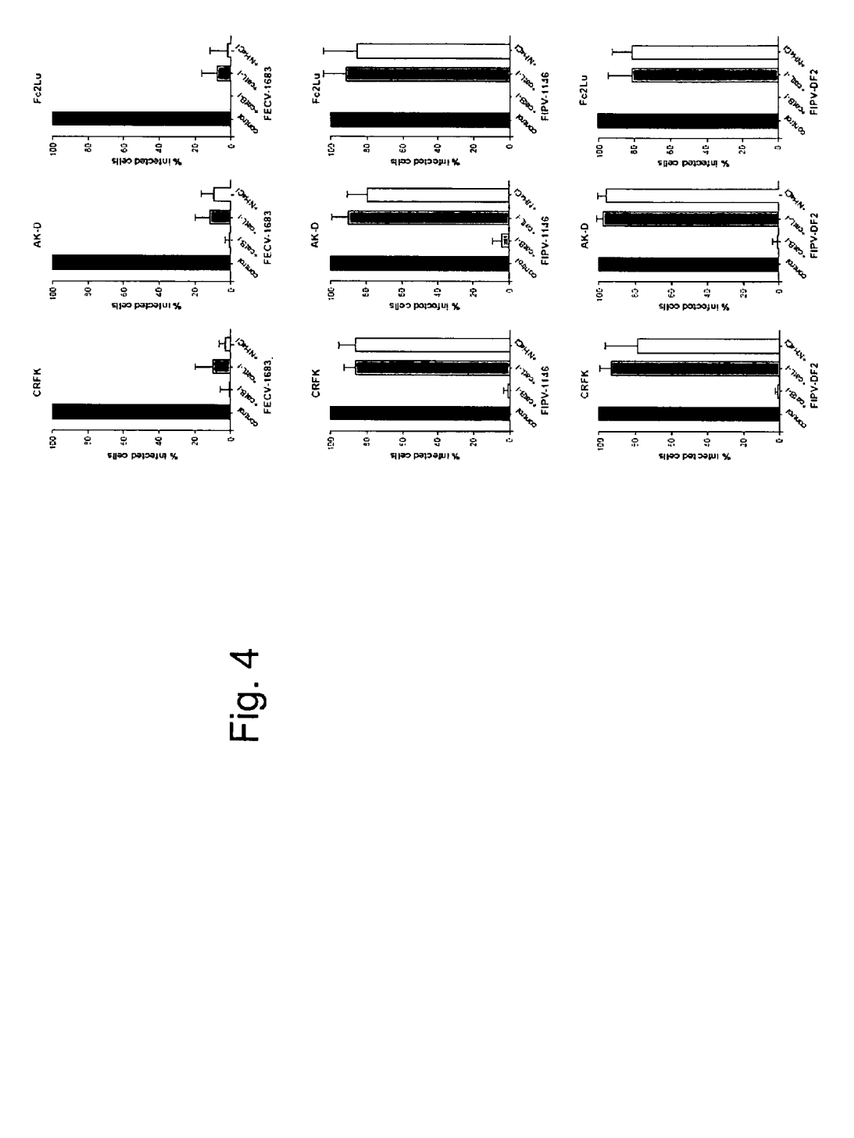

This Example demonstrates that cathepsins and low pH play a general role for serotype II feline coronavirus infection of multiple cell types. To determine whether the effects of low pH and cathepsin inhibitors were more generally applicable to serotype II coronavirus infections, we repeated key experiments using an additional feline coronavirus strain (FIPV-DF2), and also tested a variety of established feline cell lines (CRFK, AK-D and FC2Lu). As shown in FIG. 4, the results were consistent with our previous data (see FIGS. 1 and 2). The cathepsin B inhibitor CA074-Me almost completely prevented infection of all the feline coronaviruses tested, whereas the cathepsin L inhibitor Z-FY-(tBu)-DMK, selectively inhibited FECV-1683, but showed little or no effect on infection by FIPV-1146 or FIPV-DF2. Likewise, the weak base NH₄Cl selectively inhibited FECV-1683 in all the cell lines tested, but showed only a marginal effect of the FIPV biotypes.

Example 6

Figure 5:
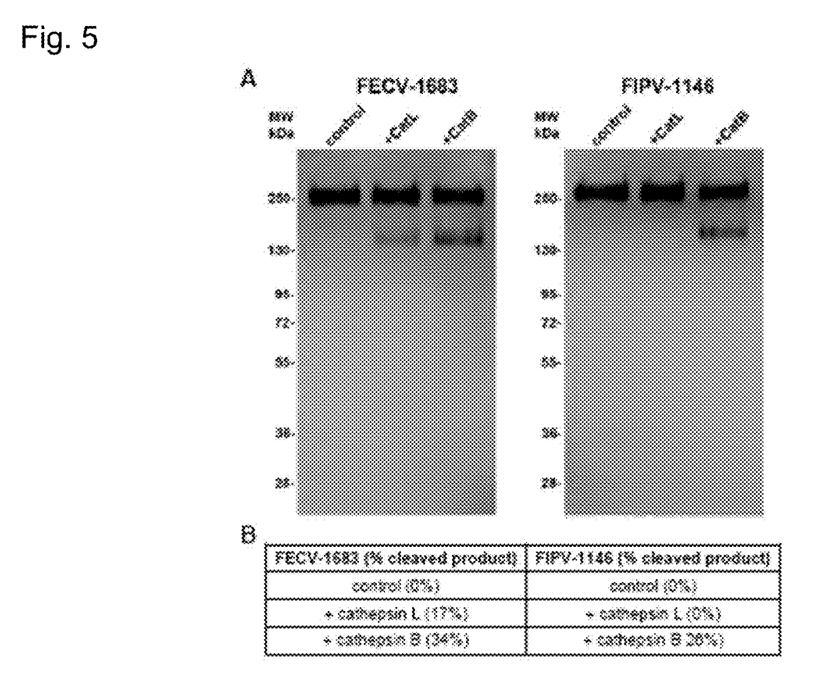

This Example demonstrates that cathepsin L selectively cleaves the S protein of FECV-1683, whereas cathepsin B can cleave the S protein of both FECV-1683 and FIPV-1146. To investigate whether the effect of cathepsins B and L occurred at the level of spike protein cleavage, concentrated FIPV-1146 and FECV-1683 viral particles were incubated with purified, activated cathepsin B and cathepsin L for 1 hour at 37° C., and then analyzed by western blot with the anti-FcoV monoclonal antibody 22G6.4, specific for the S protein. As shown in FIG. 5, cathepsin L was unable to cleave the spike protein of FIPV-1146 under the conditions tested, but was clearly able to cleave the FECV-1683 spike protein, with an obvious cleavage product of approximately 150-160 kDa. In contrast, cathepsin B was able to cleave both FIPV-1146 and FECV-1683 spike proteins, also producing a cleavage product of approximately 150-160 kDa (FIG. 5). The samples shown in FIG. 5 were pretreated with the endoglycosidase PNGase F, which resulted in a clearer representation of the cleaved product by western blot, compared to samples without PNGaseF pre-treatment, most likely due to heterogenous glycosylation of the spike protein in samples without the glycosidase (data not shown). Overall, these data indicate that cathepsin L selectively cleaves the S protein of FECV-1683, whereas cathepsin B can cleave the S protein of both FECV-1683 and FIPV-1146.

Example 7

Figure 6:
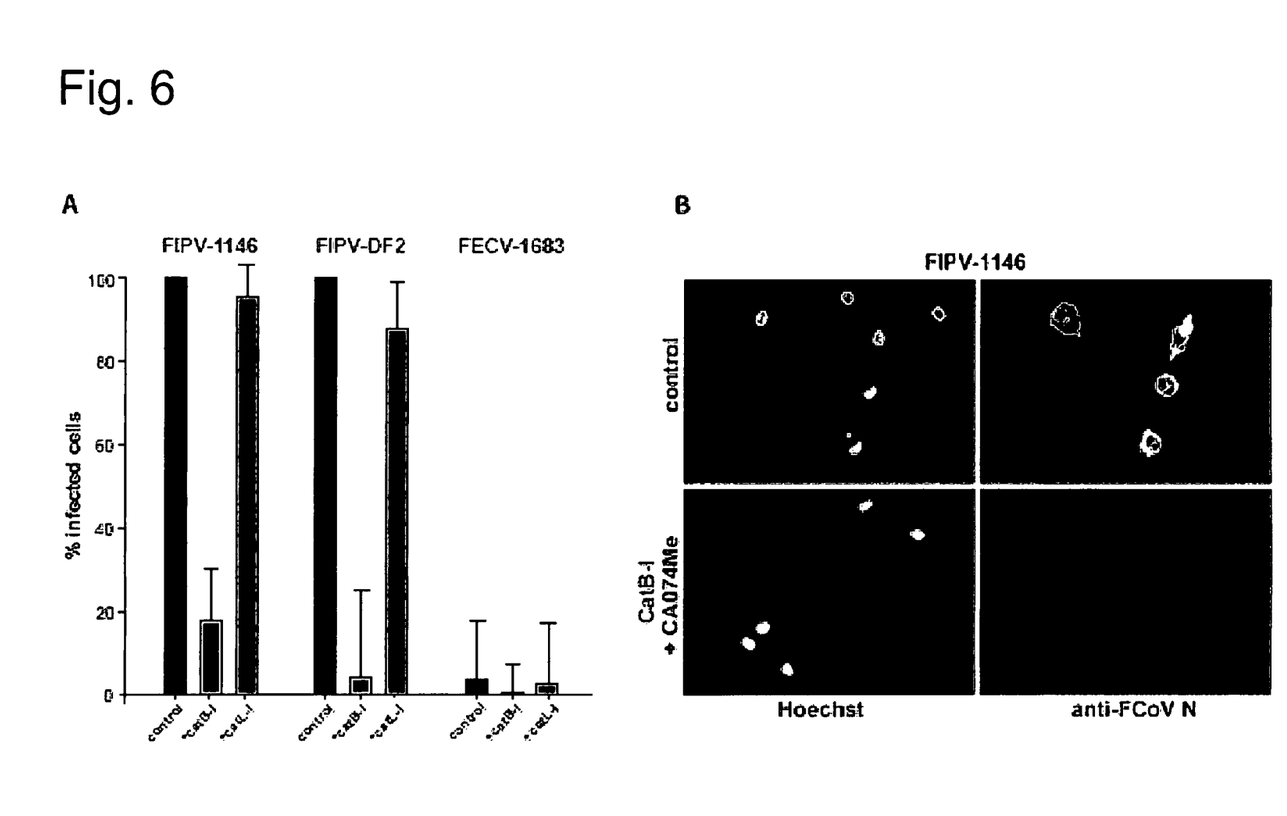

This Example illustrates the effect of inhibitors of cathepsins B and L on the infection of serotype II feline coronavirus in primary feline blood monocytes. In connection with this, the in vivo targets of the highly virulent coronaviruses FIPV-1146 and FIPV-DF2 include feline monocytes and macrophages. In order to assess whether cathepsins B and L might play a role in the entry of FIPV-1146 and FIPV-DF2 into its in vivo target, and therefore whether cathepsin inhibitors could be used to prevent infection, we isolated CD172a-positive, primary feline blood monocytes, pretreated the cells with the cathepsin B inhibitor CA074-Me, or the cathepsin L inhibitor Z-FY-(tBu)-DMK, and then infected them with FIPV-1146 or FIPV-DF2. As shown in FIG. 6, the cathepsin B inhibitor significantly reduced infection by FIPV-1146 and FIPV-DF2 (approximately 85-95% inhibition). In line with our data using cell lines, the cathepsin L inhibitor showed no significant effect on FIPV infection of primary feline monocytes. As expected (Dewerchin et al., 2005), primary feline blood monocytes were only negligibly susceptible to infection with FECV-1683, hence a role for cathepsin B or L cannot be determined in this case (FIG. 6). Thus, use of a selective cathepsin B inhibitor (but not a selective cathepsin L inhibitor) inhibits FIPV infection of primary feline blood monocytes.

Example 8

Figure 7:
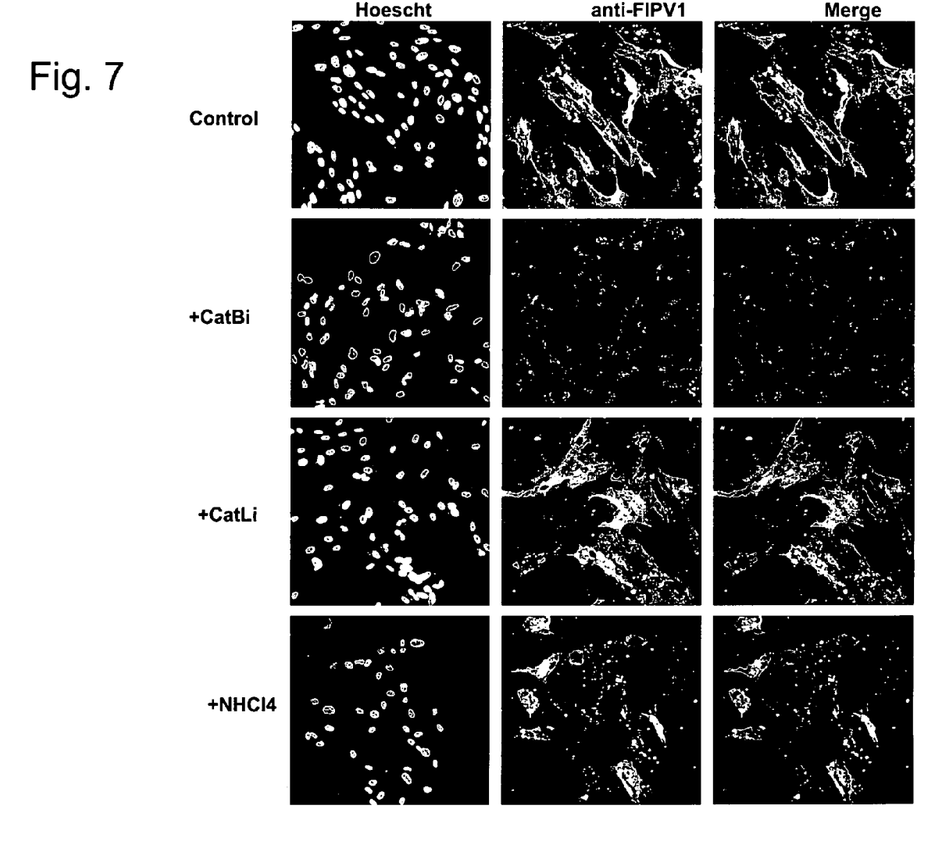
FIG. 7 demonstrates the effects of cathepsin L and cathepsin B inhibitors on infection of feline cells by a serotype I FCoV. AK-D cells were pretreated with either 10 uM cathepsin B inhibitor CA074-Me (CatB-I), 10 uM cathepsin L inhibitor Z-FY(tBu)-DMK (CatL-I), or 10 mM NH4Cl, and then infected with virus the serotype I FIPV black strain. Immunofluorescence was performed essentially as described for FIG. 4.

FIG. 7 demonstrates the effects of cathepsin L and cathepsin B inhibitors on infection of feline cells by a serotype I FCoV. AK-D cells were pretreated with either 10 uM cathepsin B inhibitor CA074-Me (CatB-I), 10 uM cathepsin L inhibitor Z-FY(tBu)-DMK (CatL-I), or 10 mM NH4Cl, and then infected with virus FIPV black strain, a serotype I FIPV. Immunofluorescence was performed essentially as described for FIG. 4. The data demonstrate that a selective cathepsin B inhibitor alone can inhibit replication of the serotype I FIPV strain.

While the invention has been described through illustrative examples, routine modifications will be apparent to those skilled in the art, which modifications are intended to be within the scope of the invention.

We claim:

1. A method for treatment of Feline infectious peritonitis (FIP) comprising administering to a cat infected with feline infectious peritonitis virus (FIPV) an effective amount of a selective cathepsin B inhibitor such that at least one FIP symptom selected from the group consisting of: fluctuating fever that is unresponsive to antibiotics or corticosteroids, effusion, peritoneal inflammation, vomiting, diarrhea, icterus, and combinations thereof, is reduced, wherein the selective cathepsin B inhibitor is (2S,3S)-trans-Epoxysuccinyl-L-leucylamido-3-methylbutane ethyl ester loxistatin (E-64d), [L-3-trans-(Propylcarbamoyl)oxirane-2-carbonyl]-L-isoleucyl-L-proline (CA074), or [L-3-trans-(Propylcarbamoyl)oxirane-2-carbonyl]-L-isoleucyl-L-proline Methyl Ester (CA074-Me).

2. The method of claim 1 comprising administering the selective cathepsin B inhibitor to the cat at least once daily for a period of at least one week.

3. The method of claim 1, further comprising the step of administering to the cat a steroid, an interferon, or combinations thereof.

4. The method of claim 1, wherein the selective cathepsin B inhibitor is selected from the group consisting of CA074 and CA074-Me, and combinations thereof.

5. The method of claim 1, comprising administering the selective cathepsin B inhibitor as a dosage of between 1 and 100 mg/kg body weight.

6. The method of claim 5, comprising administering the selective cathepsin B inhibitor as a dosage of between 5 mg/kg body weight and 25 mg/kg body weight.

* * * * *